United States Patent [19]

Fujimoto et al.

[11] Patent Number: 5,248,807
[45] Date of Patent: Sep. 28, 1993

[54] TRITERPENE DERIVATIVES

[75] Inventors: Masafumi Fujimoto; Kensuke Sakurai, both of Nara; Shinichi Mihara, Nara; Miharu Nakamura, Hyogo; Toshiro Konoike, Osaka, all of Japan

[73] Assignee: Shionogi & Co., Ltd., Osaka, Japan

[21] Appl. No.: 867,683

[22] PCT Filed: Dec. 13, 1991

[86] PCT No.: PCT/JP91/01707
§ 371 Date: Jul. 8, 1992
§ 102(e) Date: Jul. 8, 1992

[87] PCT Pub. No.: WO92/12991
PCT Pub. Date: Aug. 6, 1992

[30] Foreign Application Priority Data

Jan. 29, 1991 [JP] Japan .................. 3-029372

[51] Int. Cl.$^5$ .............................. C07C 69/76
[52] U.S. Cl. ........................ 560/75; 560/104; 560/56; 560/100; 560/9; 560/11; 560/11; 562/498; 558/179
[58] Field of Search .............. 560/104, 75, 56, 100, 560/9, 11; 562/498; 558/179; 514/533

[56] References Cited

PUBLICATIONS

Siddigui, S. et al., J. Chem. Soc. Pak. 13(2) 115–19, 1991.

Siddigui S. et al., J. Nat. Prod., 53(5) 1332–6, 1990.

Budzikiewicz, H. et al., Z. Naturforsch, B: Anorg. Chem., Org. Chem. 35B (2), 226–32 1980.

*Primary Examiner*—Paul J. Killos
*Attorney, Agent, or Firm*—Wenderoth, Lind & Ponack

[57] ABSTRACT

The present invention provides triterpene derivatives of the following formula:

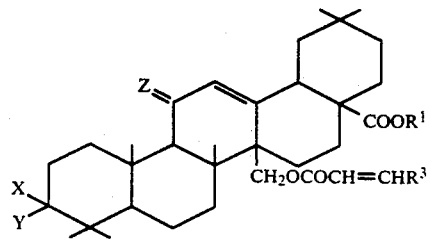

wherein, $R^1$ is hydrogen or metabolic ester-residue; $R^3$ is optionally substituted aryl or optionally substituted aromatic heterocycle; X is hydrogen and Y is hydroxy or X and Y may form together oxo; Z is an oxygen or two hydrogen atoms, or the salts thereof, which have anti-endothelin activities and are useful for preventing or treating cardiovascular failure, and pharmaceutical compositions thereof.

10 Claims, No Drawings

TRITERPENE DERIVATIVES

FIELD OF THE INVENTION

The present invention relates to useful compounds in the field of medicament and the use thereof, in more detail, to endothelin-receptor antagonists comprising triterpene derivatives which are useful for preventing or treating diseases caused by excessive secretion of endothelin, and to novel triterpene derivatives.

BACKGROUND OF THE INVENTION

Endothelin, which has been disclosed by M. Yanagisawa et al. (Nature, 332, P411, 1988), is an endothelium-derived 21-residue vasoconstrictor peptide and supposed that excessive secretion of endothelin may be involved in various diseases, such as hypertention, coronary ischemia, encepholapathy, nephropathy, circulation failure of various organs, and asthma. In Kokai 2-273625, TXA$_2$-receptor antagonist and inhibitor of TXA$_2$-synthetic enzyme etc. are disclosed as substances capable of inhibiting the increase in intracellular calcium ion concentration, which is caused by excessive secretion of endothelin. However, nobody has reported on substance capable of specifically inhibiting actions caused by endothelin, and so development of such a new compound has been desired.

Some compounds similar to the present compounds in chemical structure have already been known, however, there has been no report on the activity of those compounds as endothelin antagonist. For example, though 27-(3,4-dihydroxycinnamoyl-oxy)-3$\beta$-hydroxyoleanolic acid which is analogous to the compounds of the present invention has been reported by J. M. Koekemore et al. in JOURNAL OF THE SOUTH AFRICAN CHEMICAL INSTITUTE (27, P131, 1974), however, which has no description about the endothelin antagonist activity.

DISCLOSURE OF THE INVENTION

After enormous research, the present inventors have found active substances capable of specifically inhibiting the binding of endothelin to endothelin-receptors, whereby they have completed the present invention. Namely, the present invention provides endothelin-receptor antagonists comprising triterpene derivatives represented by the formula (II):

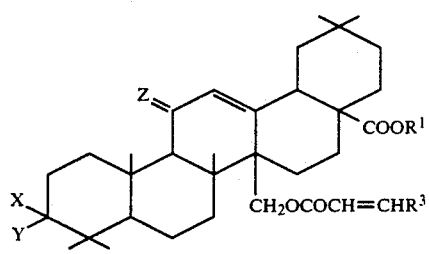

(II)

wherein, R$^1$ is hydrogen or metabolic ester-residue; R$^3$ is optionally substituted aryl or optionally substituted aromatic heterocycle; X is hydrogen and Y is hydroxy or X and Y may form together oxo; Z is an oxygen or two hydrogen atoms, or the salts thereof.

Triterpene derivatives represented by the formula (I):

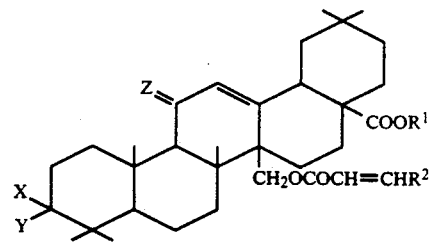

(I)

wherein, R$^1$ is hydrogen or metabolic ester-residue; R$^2$ is optionally substituted aryl or optionally substituted aromatic heterocycle; X is hydrogen and Y is hydroxy or X and Y may form together oxo; Z is an oxygen or two hydrogen atoms, provided that R$^2$ is not 3,4-dihydroxyphenyl when R$^1$ is hydrogen and Y is hydroxy, and the salts thereof are novel compounds and the present invention provides also these compounds.

In the present specification, "metabolic ester-residue" means ester-residue which decomposes to reproduce carboxylic acids in a living body. "Aryl" means phenyl or ($\alpha$-or $\beta$-) naphthyl. "Aromatic heterocycle" means aromatic 5-or 6-membered ring which contains one or more atoms selected from oxygen, sulfur, and/or nitrogen and may be condensed with carbon-cycle or another heterocycle, and N-or S-oxide of the aromatic heterocycle is included in this definition. The substituent meant in the phrase "optionally substituted" includes, for example, halogen (F, Cl, Br, I), hydroxy, amino, amino substituted by lower alkanoyl, amino substituted by mono-or di-lower alkyl, carboxy, cyano, nitro, lower alkyl, lower alkoxy, and lower alkanoyloxy. In the case either X or Y is hydroxy, the hydroxy may be in $\alpha$-or $\beta$-form.

Furthermore, in the case R$^1$ is hydrogen, the present compounds may form salts with alkali metals (sodium, potassium etc.) alkaline earth metals (calcium, magnesium etc.) ammonia or an organic base (triethylammonium etc.).

The triterpene derivatives of the present invention are able to be extracted from Myrica cerifera L. by the following method for example. Namely, branches of the plant are subjected to extraction, in room temperature for a number of days, with a polor solvent including, e.g. alcohol such as methanol, ethanol, isopropanol, n-butanol, sec-butanol, and tert-butanol, acetone, and acetonitrile etc., then to extraction with an organic solvent hardly miscible with water, which includes chlorinated hydrocarbon such as chloroform, dichloromethane, ethyl acetate, and n-butanol etc. The eluate was separated with silica gel chromatography to obtain some compounds of the present invention. Furthermore, thus obtained compounds were used as materials to prepare the other present compounds having various substituents as R$^2$.

The present compounds are useful for preventing and treating cardiovascular diseases such as vasoconstriction, hypertention, or the like because of their endothelin-receptor antagonist activity.

According to the usual methods, the present compounds are able to be formulated, together with a proper kind of carries, diluents, excipients etc., into compositions for administration via injection, oral and anal administration, or the like.

Though the dosage is not generally regulated because it changes depending on the objective effects of treatment, the administration method, or the age or weight of patient, the daily dosage is usually in the range from 10 mg to 2 g, preferably from 50 mg to 1 g, for an adult.

THE PREFERRED EMBODIMENTS OF THE INVENTION

Though the present invention is further explained by the following Examples and Experiments, which are not intended to limit the scope of the present invention at all.

EXAMPLE 1

Preparation of Compounds 1 and 2

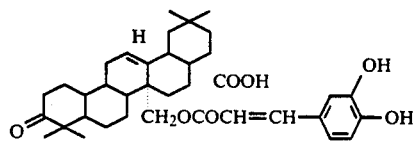

Compound 1

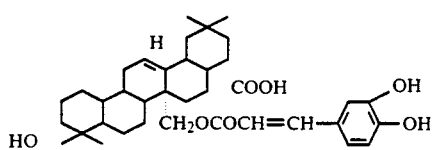

Compound 2

One kg of twigs of Myrica cerifera was pulverized, and soaked in 2 L of methanol, then allowed to stand at room temperature for 6 days. The mixture was filtrated, then the filtrate was evaporated under reduced pressure. This process was recycled 3 times to obtain 75.4 g of residue as coarse extra, 71 g of which was distributed into chloroform (500 ml×3) and water (1 L) to obtain 10 g of extract soluble to chloroform. The extract was subjected to chromatography with 130 g of silica gel (230 to 400 mesh) containing 10% water, and eluted with chloroform and methanol mixed with chloroform. The portion eluted with a mixed solution of chloroform and methanol (98:2) was again subjected to the same chromatography, then the eluate (318 mg) was subjected to high performance liquid chromatography with the column: DEVELOSIL ODS-10/20 (20 mm×250 mm). The moving layer was a mixed solution of methanol and water (9:1) at flow rate of 3 ml/min. An ordinary differential refractometer was used for the detection of the objective compounds. The retention time was 28 min. The eluted compounds were purified by recycling the method 3 to 5 times, whereby the objective esters were obtained.

Compound 1

Yield: 103 mg Molecular Formula: $C_{39}H_{52}O_7$ (m/z 632) mp. 177°–182° C. $[\alpha]_D + 149.4 \pm 2.2°$ (25° C., c 0.88, MeOH).

$^1$H-NMR δ ppm (CDCl$_3$): 7.49(1H, d, J=15.8 Hz), 7.05(1H, d, J=1.5 Hz), 6.92(1H, dd, J=1.5, 8.3 Hz), 6.85(1H, d, J=8.3 Hz), 6.16(1H, d, J=15.8 Hz), 5.64(1H, t, J=3.2 Hz), 4.36(1H, d, J=12.7 Hz), 4.16(1H, d, J=12.7 Hz), 2.93(1H, dd, J=3.8, 13.6 Hz), 2.51-2.35(2H, m), 1.08, 1.04(×2), 0.93, 0.86, 0.84(3H each, s).

$^{13}$C-NMR δ ppm (CDCl$_3$): 219.3, 181.3, 167.8, 147.8, 145.6, 145.3, 137.7, 126.9, 126.8, 122.1, 115.5, 115.0, 114.2, 65.6, 55.0, 47.9, 47.5, 46.4, 45.6, 44.9, 41.3, 40.0, 39.1, 37.0, 34.1, 33.6, 33.0, 32.7, 32.5, 30.7, 26.7, 24.1, 23.6, 23.6, 22.9, 21.5, 19.7, 17.9, 15.3.

Compound 2

Amorphous, Molecular Formula: $C_{39}H_{54}O_7$, MS (SIMS Method) m/e 657[M+Na]$^+$ $[\alpha]_D + 170.4 \pm 1.6°$ (22° C., C=1.30, MeOH).

$^1$H-NMR δ ppm (CD$_3$OD): 7.50(1H, d, J=16.2 Hz), 7.01(1H, d, J=1.6 Hz), 6.91(1H, dd, J=8.2, 1.6 Hz), 6.79(1H, d, J=8.2 Hz), 6.17(1H, d, J=16.2 Hz), 5.61(1H, m), 4.41(1H, d, J=12.4 Hz), 4.14(1H, d, J=12.4 Hz), 3.11(1H, m), 2.94(1H, br.d, J=11.0 Hz), 0.77, 0.83, 0.94, 0.96(×3) (3H each, s).

$^{13}$CNMR δ ppm (CD$_3$OD): 181.7, 168.8, 149.7, 146.9, 146.9, 138.9, 128.1, 127.5, 122.8, 116.6, 115.3, 115.0, 79.5, 66.7, 56.6, 50.0, 47.3, 46.6, 46.2, 42.5, 41.2, 39.8, 39.7, 38.3, 34.7, 34.4, 33.7, 33.5, 31.5, 28.7, 27.8, 25.1, 24.7, 24.1, 23.9, 19.5, 18.9, 16.3, 16.1.

REFERENCE EXAMPLE 1

Preparation of Compound A

Compound 1 ⟶

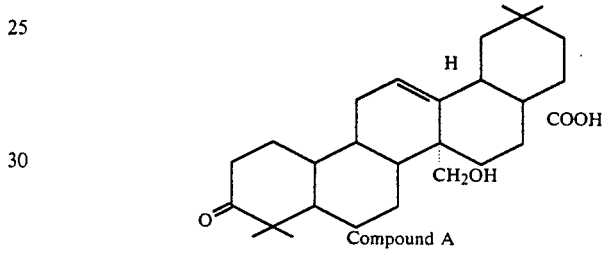

Compound A

Compound 1 (110.0 mg) was dissolved into 4 ml of a solution of 3% KOH dissolved into methanol, and the mixture was heated under reflux for 3 hours. Water was added thereto, from which methanol was evaporated under reduced pressure. The resulting solution was acidified with 1N sulfuric acid, extracted with ethyl acetate (15 ml×3), which was washed with water and evaporated. The obtained residue was subjected to silica gel chromatography to obtain 14.6 mg of compound A from the portion of 2% methanol/chloroform. Mp. 226°–227° C. $[\alpha]_D + 91.3°$ (C=1.0, CHCl$_3$) m/e 470 ($C_{30}H_{46}O_4$).

A wide variety of compounds substituted at 27-position are prepared by applying the following methods.
(a) The direct acylation for compound A
(b) Horner-Emmons method for Compound A

(a) The Direct Acylation

Compound A is treated with acid halides (R$^2$CH=CHCO-halogen) or reactive derivatives of carboxylic acids such as [(R$^2$CH=CHCO)$_2$O)] in the presence of dimethylaminopyridine (DMAP), to give the present compounds represented by the formula (II).

(b) Horner-Emmons Method

Dimethylphosphonoacetic anhydride, which was prepared from dimethylphosphonoacetic acid and dicyclohexylcarbodiimide (DCC), is reacted with compound A in the presence of DMAP to give dimethylphosphonoacetate ester of compound A (hereinafter referred to as compound B). Compound B was condensed with aldehydes (R$^2$CHO) in the presence of either cesium carbonate or lithium chloride-triethylamine, to give Compound (I).

EXAMPLE 2

Preparation of Compound 3

Compound A ⟶

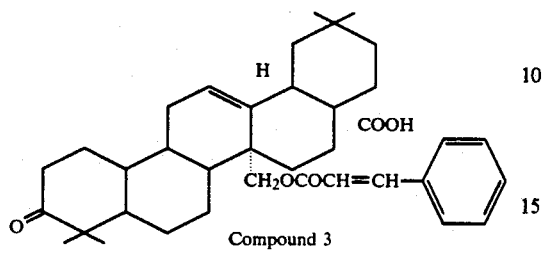

Compound 3

To a solution of 13.2 mg of compound A (0.028 mmole) dissolved into 0.6 ml of dichloromethane was added 10.3 mg of dimethylaminopyridine (DMAP, 0.0843 mg, 3 eq.), successively 11.7 mg of cinnamoyl chloride (0.07 mmole, 2.5 eq.). The mixture was allowed to stand at room temperature over night, then condensed to give solid residue. The residue was dissolved into 2 ml of THF and under ice-cooling, 1 ml of an aqueous solution of 0.1N sodium hydroxide was added to the resulting mixture and the mixture was stirred for 30 min. Hydrochloric acid was added to acidify the reaction mixture, then the resulting mixture was extracted with ethyl acetate. The organic layer was washed with water, dried over magnesium sulfate, and subjected to silica gel chromatography with hexane-ethyl acetate (2:1) as eluent, to give 15.2 mg of the objective compound 3 in 90% yield.

$^1$H-NMR δ(ppm) (CDCl$_3$):0.85(s,6H), 0.92(s,3H), 1.03(s,3H), 1.04(s,3H), 1.08(s,3H), 1.0–2.1(m,20H), 2.2–2.6(m,2H), 2.8–3.0(m,1H), 4.15,4.38 (ABq,2H, J=13.4 Hz), 5.67(br.s,1H), 6.37(br.s,1H), 7.4–7.6(m,5H), 7.62 (d,1H, J=15.8 Hz).

EXAMPLE 3

Preparation of Compound 4

Compound A ⟶

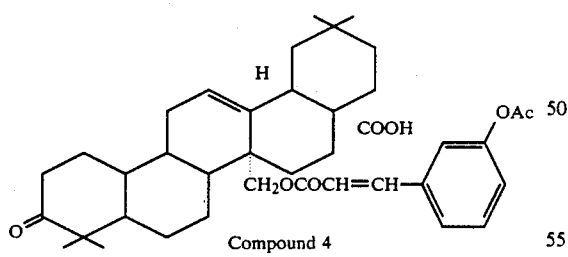

Compound 4

Compound A (5 mg, 0.0106 mmole), 5.2 mg of DMAP (4 eq.), and 13 mg of 3-acetoxycinnamic anhydride (3 eq.) were dissolved into 0.14 ml of dichloromethane, and the mixture was allowed to stand at room temperature for 3 hours. The reaction mixture was purified by using a silica gel chromatography with CHCl$_3$-MeOH as eluent, to give 4.6 mg of compound 4 in 66% yield. Rf=0.8 (CHCl$_3$: MeOH=10:1).

$^1$H-NMR δ ppm (CDCl$_3$): 0.83(s,3H), 0.85(s,3H), 0.93(s,3H), 1.02(s,3H), 1.04(s,3H), 1.08(s,3H), 1.1–2.1(m,20H), 2.34(s,3H), 2.3–2.6(m,2H), 2.8–3.0(m,1H), 4.16,4.34(ABq,2H, J=12.8 Hz), 5.65(br.s,1H), 6.34(d,1H,J=16.2 Hz), 7.1–7.2(m,1H), 7.23(br.s,2H), 7.3–7.5(m,2H), 7.59(d,1H,J=16.2 Hz).

EXAMPLE 4

Preparation of Compound 5

Compound 4 ⟶

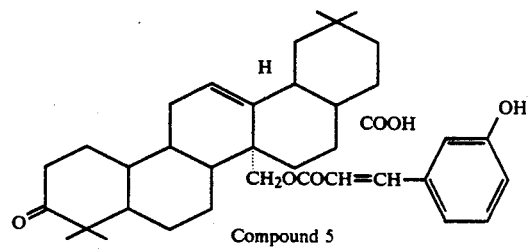

Compound 5

To a solution of 9.9 mg of compound 4 dissolved in 1 ml of methanol, a solution of 3% KOH dissolved in methanol was added under ice-cooling. The mixture was stirred for 30 min. and poured into dil. aqueous hydrochloric acid, then extracted with ethyl acetate. The organic layer was dried, condensed, and subjected to silica gel chromatography with CHCl$_3$-MeOH as eluent, to give compound 5.

Rf=0.6 (CHCl$_3$:MeOH=10:1).

$^1$H-NMR δ ppm (CDCl$_3$): 0.83(s,3H), 0.86(s,3H), 0.93(s,3H), 1.03(s,3H), 1.05(s,3H), 1.08(s,3H), 1.1–2.1(m,20H), 2.3–2.5(m,2H), 2.8–3.0(m,1H), 4.19,4.36(ABq,2H,J=13.0 Hz), 5.65(br.s,1H), 6.32(d,1H,J=7.9, 2.4, 0.8 Hz), 6.90(ddd,1H,J=7.9,2.4,0.8 Hz), 6.97(t,1H,J=1.8 Hz), 7.07(d,1H,J=7.9 Hz), 7.27(t,1H,J=7.9 Hz), 7.57(d,1H,J=15.8 Hz)

EXAMPLE 5

Preparation of Compound 6

Compound 5 ⟶

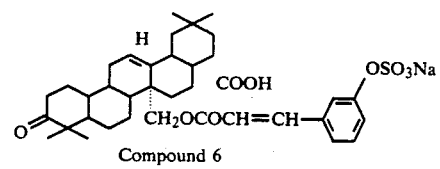

Compound 6

To a solution of 3.1 mg of compound 5 (0.005 mmole) dissolved into 50 μl of DMF was added 8 μl of 1N-NaOH, successively 1 mg of sulfur trioxide-trimethylamine complex. After repeating the process 10 times, the resulting mixture was evaporated under reduced pressure and dried to give solid residue. To the residue, 1 ml of water and 1N-NaOH were added, then the mixture was subjected to the chromatography of Diaion HP20 ® (water/MeOH:50/50), to give 1.4 mg of compound 6 in 38% yield. Rf=0.4 (ethyl acetate: acetic acid:water=30:1:1)

EXAMPLE 6

Preparation of Compound 7

Compound 5 ⟶

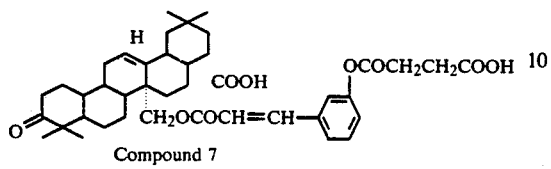

Compound 7

To a solution of 7 mg of compound 5 (0.0011 mmole) dissolved in 0.1 ml of dichloromethane, 11 mg of DMAP (8 eq.) and 6.6 mg of succinic anhydride (6 eq.) were added thereto and the mixture was stirred in room temperature for 5 hours. The reaction mixture was poured into dil. hydrochloric acid and extracted with ethyl acetate. The extracts were dried, evaporated, and subjected to silica gel chromatography ($CHCl_3$:MeOH=10:1), to give 3.1 mg of compound 7 in 39% yield. Rf=0.4 ($CHCl_3$:MeOH=10:1).

$^1$H-NMR δ ppm ($CDCl_3$): 0.83(s,3H), 0.86(s,3H), 0.93(s,3H), 1.04(s,3H), 1.05(s,3H), 1.08(s,3H), 1.0–2.1(m,20H), 2.2–2.8(m,2H), 2.8–3.0(m,3H), 4.2–4.4(m,2H), 5.63(br.s.1H), 6.32(d,1H,J=16.0 Hz), 7.1–7.4(m,4H), 7.58 (d,1H,J=16.0 Hz).

EXAMPLE 7

Preparation of Compound 8

Compound A ⟶

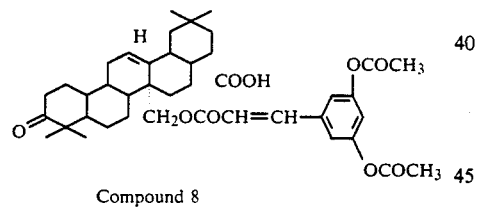

Compound 8

To a solution of 5.0 mg of compound A (0.011 mmole) dissolved into 0.15 ml of dichloromethane was added 5.2 mg of DMAP (4 eq.), successively 10 mg of 3,5-diacetoxycinnamoyl chloride (3 eq.). The mixture was allowed to stand at room temperature for 2 hours and the reaction solution was evaporated and dried to obtain its solid, which was dissolved into 1 ml of THF. Under ice-cooling, 1 ml of an aqueous solution of 0.1N sodium hydroxide was added thereto and the resulting mixture was stirred for 30 min. The reaction solution was aidified with 0.1N HCl and subjected to extraction with ethyl acetate. The organic layer was washed with water, dried over anhydrous magnesiumsulfate, evaporated, and subjected to silica gel chromatography, to give 1.9 mg of compound 8 in 25% yield. $^1$H-NMR δ ppm ($CDCl_3$): 0.82(s,3H), 0.86(s,3H), 0.93(s,3H), 1.04(s,6H), 1.09 (s,3H), 1.0–2.1(m,20H), 2.2–2.8(m,2H), 2.31(s,6H), 2.8–3.0(m,1H), 4.15, 4.38(ABq,2H,J=16.0 Hz), 5.67(br.s,1H), 6.29(d,1H,J=16.0 Hz), 6.66 (t,1H,J=2.0 Hz), 6.81(s,2H), 7.54(d,1H,J=16.0 Hz).

EXAMPLE 8

Preparation of Compound 9

Compound 8 ⟶

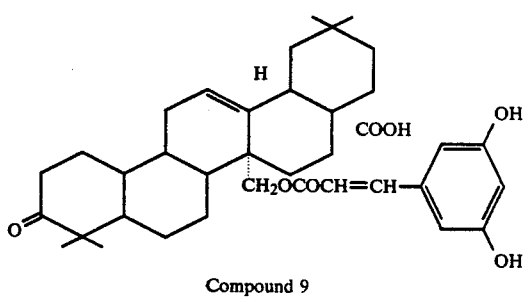

Compound 9

To a solution of 1.9 mg of compound 8 (0.003 mmole) dissolved into 0.5 ml of methanol, 0.1 ml of a solution of 3% KOH dissolved into methanol was added under ice-cooling and the resulting mixture was stirred for 30 min. The reaction solution was acidified with 1N HCl, then extracted with ethyl acetate. The organic layer was washed with water, dried over anhydrous magnesium sulfate, evaporated, and subjected to silica gel chromatography, to give 0.4 mg of compound 9 in 24% yield.

$^1$HNMR δ ppm ($CD_3OD$):0.85(s,3H), 0.90(s,3H), 0.94(s,3H), 1.04(s,3H), 1.07 (s,6H), 1.1–2.1(m,20H), 2.2–2.7(m,2H), 2.9–3.1(m,1H), 4.17,4.18 (ABq, 2H, J=13.0 Hz), 5.63(br.s,1H), 6.27(d,1H, J=16.0 Hz), 6.30(t,1H,J=2.0 Hz), 6.46(d,2H,J=2.2 Hz), 7.54(d,1H,J=16.0 Hz).

REFERENCE EXAMPLE 2

Preparation of dimethoxyphosphonoacetic anhydride

To a solution of 1.68 g of dimethoxyphosphonoacetic acid (10 mmole) dissolved into THF, 980 mg of DCC (4.75 mmole) was added. The mixture was stirred at room temperature for 8 hours and 20 ml of ether was added thereto, then the resulting solution was allowed to stand at −20° C. The precipitate was removed by filtration, whereby the solution of dimethoxyphosphonoacetic anhydride was obtained (calcd. yield: 0.11 mole/l).

REFERENCE EXAMPLE 3

Preparation of Compound B

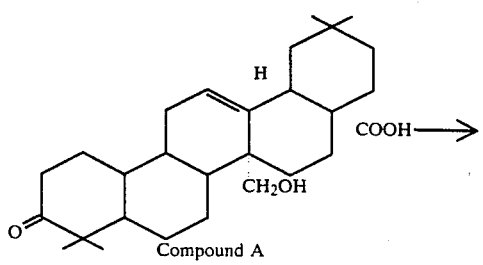

Compound A

-continued

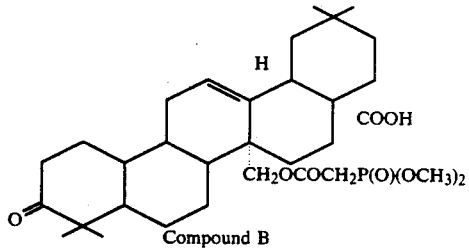
Compound B

To a mixture of 15.6 mg of compound A (0.033 mmole) with 16 mg of DMAP (4 eq.) was added 1.2 ml of the above solution of dimethoxyphosphonoacetic anhydride (4 eq.). Dichloromethane (0.3 ml) was added thereto and the resulting mixture was stirred at room temperature for 5 hours, then subjected to extraction with ethyl acetate. The extracts were, evaporated, and purified by using a silica gel chromatography (CHCl$_3$:MeOH=20:1), to give 13.3 mg of compound B in 65% yield.

$^1$H-NMR δ ppm (CDCl$_3$): 0.81(s,3H), 0.89(s,3H), 0.94(s,3H), 1.03(s,3H), 1.04(s,3H), 1.09(s,3H), 1.1-2.1(m,20H), 2.2-2.7(m,2H), 2.8-3.0(m,1H), 2.95(d,2H,J=21.8 Hz), 3.81(d,6H,J=11.2 Hz), 4.15,4.33(ABq,2H,J=12.8 Hz), 5.61(br.s,1H).

EXAMPLE 9

Preparation of Compounds 10 and 11

Compound B——>

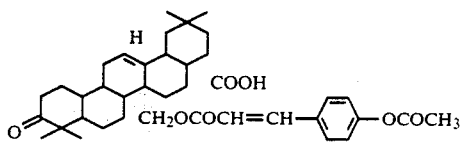
Compound 10

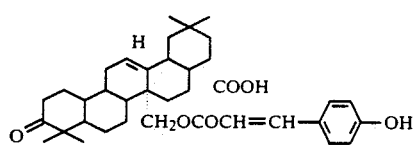
Compound 11

To a solution of 2.76 mg of compound B dissolved in 0.1 ml of 2-propanol was added 2.5μl of 4-acetoxybenzaldehyde (4 eq.), successively 3 mg of cesium carbonate, and the mixture was stirred at room temperature for 30 min. The reaction mixture was poured into dil. hydrochloric acid and extracted with ethyl acetate. The organic layer was evaporated and subjected to a silica gel chromatography (CHCl$_3$: MeOH=100:1-20:1), to give 1.1 mg of compound 10 [Rf=0.8 (CHCl$_3$: MeOH=10:1)] and 1.0 mg of compound 11 [Rf=0.6 (CHCl$_3$: MeOH=10:1)] were obtained.

Compound 10

$^1$HNMR δ ppm (CDCl$_3$): 0.84(s,3H), 0.85(s,3H), 0.93(s,3H), 1.02(s,3H), 1.04(s,3H), 1.08(s,3H), 1.0-2.1(m,20H), 2.32(s,3H), 2.3-2.6(m,2H), 2.8-3.0(m,1H), 4.15,4.38(ABq,2H,J=12.6 Hz), 5.66(br,s,1H), 6.3(d,1H,J=15.8 Hz), 7.13(d,1H,J=8.6 Hz), 7.54(d,2H,J=8.6 Hz), 7.60(d,1H,J=15.8 Hz).

Compound 11

$^1$H-NMR δ ppm (CDCl$_3$): 0.84(s,3H), 0.85(s,3H), 0.93(s,3H), 1.03(s,3H), 1.04(s,3H), 1.07(s,3H), 1.0-2.1(m,20H), 2.2-2.6(m,2H), 2.8-3.0(m,1H), 4.13,4.37(ABq,2H,J=12.6 Hz), 5.65(br,s,1H), 6.22(d,1H,J=15.8 Hz), 6.84(d,2H,J=8.4), 7.41(d,2H,J=8.4 Hz), 7.56(d,1H,J=15.8 Hz).

EXAMPLE 10

Preparation of Compound 12

Compound B——>

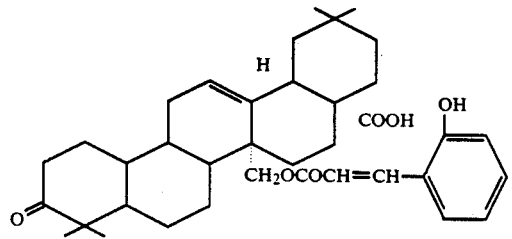
Compound 12

To a solution of 2.76 mg of compound B and 1.4μl of 2-hydroxybenzaldehyde (3 eq.) dissolved into 0.1 ml of isopropanol, 3 mg of cesium carbonate was added. The mixture was stirred at room temperature for 30 min. and subjected to extraction with ethyl acetate. The organic layer was washed with water, dried, and subjected to a silica gel chromatography (CHCl$_3$:MeOH=100:1-20:1), to give 1.7 mg of compound 12 was obtained. Rf=0.5 (CHCl$_3$:MeOH=10:1).

$^1$H-NMR δ ppm (CDCl$_3$):0.84(s,3H), 0.85(s,3H), 0.92(s,3H), 1.03(s,6H), 1.08(s,3H), 1.1-2.2(m,20H), 2.2-2.6(n,2H), 2.8-3.0(m,1H), 4.19,4.36(ABq,2H,J=12.8 Hz), 5.66(br,s,1H), 6.46(d,1H,J=14.0 Hz), 6.63(dd,1H,J=8.0, 1.0 Hz), 6.95(t,1H,J=8.0), 7.2-7.3(m,1H), 7.49(dd,1h,J=8.0, 1.0), 7.92(d,1H,J=14.0 Hz).

EXAMPLE 11

Preparation of Compound 13

Compound B——>

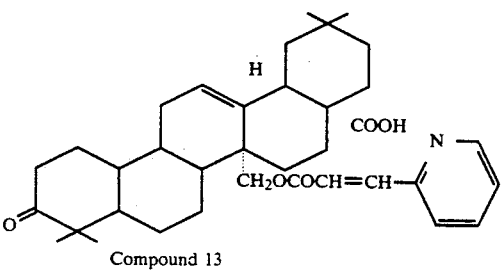
Compound 13

To a solution of 33.7 mg of compound B dissolved into 0.9 ml of acetonitrile were added 17 μl of triethylamine (2.2 eq.), 5.7 μl of 2-pyridinecarboxaldehyde (1.1 eq.) and 5.2 mg of lithium bromide (1.1 eq.), then the mixture was stirred at room temperature for 1 hour. The reaction mixture was evaporated and subjected to a silica gel chromatography (CHCl₃:MeOH=50:1), to gige 14.6 mg of compound 13 was obtained in 75% yield. Rf=0.6 (CHCl₃:MeOH=10:1).

¹H-NMR δ ppm (CDCl₃):0.83(s,3H), 0.86(s,3H), 0.93(s,3H), 1.01(s,3H), 1.03(s,3H), 1.07(s,3H), 1.1-2.1(m,20H), 2.2-2.6(m,2H), 2.8-3.0(m,1H), 4.19, 4.40(ABq,2H,J=13.0 Hz), 5.66(br.s,1H), 6.86(d,1H, J=15.6 Hz), 7.2-7.4(m,1H), 7.44(d,1H,J=5.6 Hz), 7.64(d,1H,J=15.6 Hz), 7.76(td,J=7.6, 2.0 Hz), 8.2-8.3(m,1H).

EXAMPLE 12

Preparation of Compound 14

¹H-NMR δ ppm (CDCl₃): 0.86(s,3H), 0.96(s,3H), 1.05(s,3H), 1.06(s,3H), 1.09(s,3H), 1.20(s,3H), 1.1-2.1(m,20H), 2.2-2.6(m,2H), 2.8-3.0(m,1H), 4.45 4.5(ABq,2H,J=13.0 Hz), 5.99(s,1H), 6.34(d,1H,J=16.0 Hz), 7.1-7.2(m,1H), 7.23(br,s,1H), 7.3-7.5(m,2H), 7.59(d,1H,J=16.0 Hz)

It has been supposed that endothelin relates to cardiovascular failure, because it shows a wide variety of pharmacological effects, e.g., smooth muscle constriction, by activating its specific receptors existing on cell membranes at various organs such as blood vessels or trachea. The following Experimental Examples show the anti-endothelin activity of the present compounds.

EXPERIMENTAL EXAMPLE 1

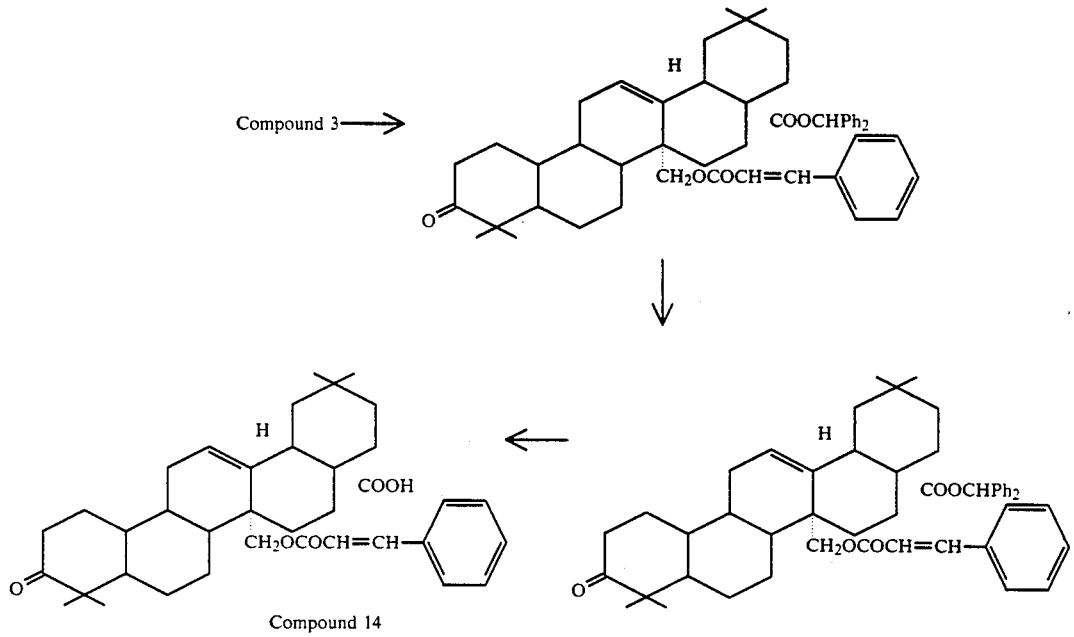

Compound 14

To a solution of 4.0 mg of compound 3 (0.007 mmole) dissolved in 8 μl of dichloromethane, 5.2 mg of diphenyldiazomethane (4 eq.) was added and the mixture was stirred at room temperature over night. A drop of acetic acid was added thereto and the resulting solution was stirred for 30 min., then evaporated and dried to obtain its solid, which was separated and purified with silica gel chromatography (hexane:ethyl acetate=4:1), to give 5 mg of the diphenylmethyl ester of compound 3. To a solution of 5 mg of the ester (0.007 mmole) dissolved into 15 μl of benzene were added a catalitic pulverized Molecular Sieves (4A) and 36 mg of pyridiniumchloroformate (PCC) (4 eq.) and the mixture was heated under reflux for 24 hours. The resulting solution was evaporated and dried to obtain its solid, which was separated and purified by using a silica gel chromatography (hexane:ethyl acetate=4:1), to give the diphenylmethyl ester of compound 14 was obtained.

To a solution of the above ester of compound 14 dissolved into 100 μl of dichloromethane were added 20 μl of anisole and 80 μl of trifluoroacetic acid, then the mixture was stirred for 30 min. The resulting solution was evaporated to dryness to give solid residue, which was separated and purified by using a silica gel chromatography (CHCl₃/MeOH), to give 0.1 mg of compound 14 was obtained.

Inhibitory Effect on the Binding of ¹²⁵I-Endothelin-1 to the Receptor

Method

Membrane fractions were prepared from porcine and rat hearts, rat thoracic aorta, and the media of porcine aorta. Each membrane fraction was incubated, in the presence or absence of the present compound 1 with 25 pM of ¹²⁵I-endothelin-1 at 37° C. for 1 hour. After the reaction was completed, ¹²⁵I-endothelin-1 bound to each membrane fraction was separated by rapid filtration through glass fiber filters and its radioactivity was determined with a gamma-counter. The specific binding was calculated by subtracting, from the total binding, the non-specific binding which was determined in the presence of $10^{-7}$M of non-radioactive endothelin-1. The concentration of the present compound 1 to inhibit 50% of the specific binding (i.e., IC₅₀) is shown at Table 1.

TABLE 1

| Kind of Membrane Ingredient | IC₅₀ (nM) |
| --- | --- |
| the media from porcine aorta | $3.2 \times 10^{-8}$ |
| porcine heart | $8.3 \times 10^{-8}$ |
| rat aorta | $5.6 \times 10^{-8}$ |

EXPERIMENTAL EXAMPLE 2

Inhibition of the endothelin-1-induced increase in cytosolic calcium ion concentration

Method

To a cuvette was put the suspension of rat aortic smooth muscle A7r5 cells, obtained from Dainippon Pharmaceutical Co., Ltd., loaded with 2 μM of fura-2 (Dojindo), then the change in fluorescence intensity was determined with a calcium analizer (CAF100, Nippon Bunkou Co.). In the determination, the exciting was performed at 340 nm and 380 nm and the recording at 510 nm. Calculation for the concentration of cytosolic calcium ion was performed according to the method of Grynkiewicz et al. (J.Biol.Chem., 260, P. 3440-3450, 1985). The experiment was performed as follows: at first, the present compounds were added to the cell suspension in the cuvette and the mixture was incubated for 1 min. Then, $10^{-8}$M of endothelin-1 was added thereto and the change in fluorescence intensity was determined. The concentration of the present compounds to inhibit the endothelin-1-induced increase in cytosolic calcium ion by 50%, (i.e., $IC_{50}$) is shown at Table 2.

TABLE 2

| Compound No. | $IC_{50}$ ($\times 10^{-8}$) |
|---|---|
| 1 | 1.1 |
| 3 | 1.8 |
| 4 | 3.4 |
| 5 | 1.1 |
| 6 | 1.4 |
| 7 | 0.9 |
| 8 | 26.0 |
| 9 | 0.45 |
| 10 | 18.0 |
| 11 | 2.7 |
| 12 | 2.7 |
| 13 | 2.5 |
| 14 | 1.0 |

At the concentration of $10^{-6}$M, the present compounds did not show any significant effects on the actions caused by bradykinin, bonbesin, or $TXA_2$-receptor agonist.

INDUSTRIAL UTILITY

As apparent from the above results, the present compounds bind to the endothelin-receptor and specifically inhibit actions caused by endothelin. Accordingly, the present compounds are expected to show effects of preventing or treating various diseases caused by excessive secretion of endothelin, for example, hypertention, coronary ischemia, encepholapathy, nephropathy, circulation failure of various organs, and asthma.

We claim:

1. A triterpene of the following formula (I):

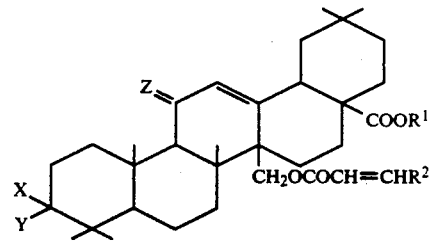

wherein, $R^1$ is hydrogen or metabolic ester-residue; $R^2$ is optionally substituted aryl or optionally substituted aromatic heterocycle; X is hydrogen and Y is hydroxy or X and Y may form together oxo; Z is an oxygen or two hydrogen atoms, provided that $R^2$ is not 3, 4-dihydroxyphenyl when $R^1$ is hydrogen and Y is hydroxy, or the salts thereof.

2. The compound claimed in claim 1, wherein $R^1$ is hydrogen; X and Y form together oxo.

3. The compound claimed in claim 1, wherein $R^2$ is phenyl, hydroxyphenyl, or dihydroxyphenyl.

4. A pharmaceutical composition containing the triterpene of the following formula (II):

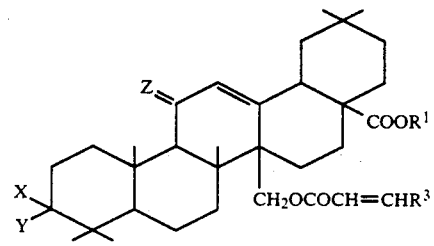

wherein, $R^1$ is hydrogen or metabolic ester-residue; $R^3$ is optionally substituted aryl or optionally substituted aromatic heterocycle; X is hydrogen and Y is hydroxy or X and Y may form together oxo; Z is an oxygen or two hydrogen atoms, or the salts thereof.

5. The pharmaceutical composition claimed in claim 4, wherein $R^1$ is hydrogen; X and Y form together oxo.

6. The pharmaceutical composition claimed in claim 4, which has antagonistic activities to endothelin-receptors.

7. The method for preventing or treating diseases caused by endothelin, which comprises administering the compound shown in claim 4.

8. The compound claimed in claim 2, wherein $R^2$ is phenyl, hydroxyphenyl, or dihydroxyphenyl.

9. The pharmaceutical composition claimed in claim 5, which has antagonistic activities to endothelin-receptors.

10. The method for preventing or treating diseases caused by endothelin, which comprise administering the compound shown in claim 4, wherein $R^1$ is hydrogen; X and Y together form oxo.

* * * * *

UNITED STATES PATENT AND TRADEMARK OFFICE
CERTIFICATE OF CORRECTION

PATENT NO. : 5,248,807
DATED : September 28, 1993
INVENTOR(S) : Masafumi FUJIMOTO, Kensuke SAKURAI, Shinichi MIHARA, Miharu NAKAMURA and Toshiro KONOIKE It is certified that error appears in the above-indentified patent and that said Letters Patent is hereby corrected as shown below:

Column 11, line 4, change "gige" to --give--, and delete "was obtained".

Signed and Sealed this

Twenty-ninth Day of November, 1994

Attest:

BRUCE LEHMAN

Attesting Officer    Commissioner of Patents and Trademarks